(12) United States Patent
Aimiya et al.

(10) Patent No.: US 10,889,720 B2
(45) Date of Patent: Jan. 12, 2021

(54) PHOSPHOR INTEGRATED DOTS NANOPARTICLES AND LABELING AGENT USING SAME

(71) Applicant: Konica Minolta, Inc., Tokyo (JP)

(72) Inventors: Takuji Aimiya, Nishitokyo (JP); Kensaku Takanashi, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 352 days.

(21) Appl. No.: 16/061,986

(22) PCT Filed: Dec. 6, 2016

(86) PCT No.: PCT/JP2016/086144
§ 371 (c)(1),
(2) Date: Jun. 13, 2018

(87) PCT Pub. No.: WO2017/104476
PCT Pub. Date: Jun. 22, 2017

(65) Prior Publication Data
US 2018/0362770 A1 Dec. 20, 2018

(30) Foreign Application Priority Data
Dec. 18, 2015 (JP) .................................. 2015-247590

(51) Int. Cl.
| | |
|---|---|
| C09B 67/02 | (2006.01) |
| C08L 101/02 | (2006.01) |
| C09B 67/08 | (2006.01) |
| C08K 5/00 | (2006.01) |
| C08L 89/00 | (2006.01) |
| C08K 5/55 | (2006.01) |
| G01N 1/30 | (2006.01) |
| G01N 33/52 | (2006.01) |
| C09K 11/06 | (2006.01) |
| C09K 11/02 | (2006.01) |
| C08J 7/12 | (2006.01) |
| C09B 11/24 | (2006.01) |
| C09B 19/00 | (2006.01) |
| C09B 29/08 | (2006.01) |
| B82Y 30/00 | (2011.01) |
| B82Y 40/00 | (2011.01) |

(52) U.S. Cl.
CPC ............. *C09B 67/0097* (2013.01); *C08J 7/12* (2013.01); *C08K 5/0041* (2013.01); *C08K 5/55* (2013.01); *C08L 89/00* (2013.01); *C08L 101/02* (2013.01); *C09B 11/24* (2013.01); *C09B 19/00* (2013.01); *C09B 29/08* (2013.01); *C09B 67/0013* (2013.01); *C09K 11/02* (2013.01); *C09K 11/06* (2013.01); *G01N 1/30* (2013.01); *G01N 33/52* (2013.01); *B82Y 30/00* (2013.01); *B82Y 40/00* (2013.01); *C08J 2300/24* (2013.01); *C09K 2211/1029* (2013.01); *C09K 2211/1033* (2013.01); *C09K 2211/1088* (2013.01); *C09K 2211/1096* (2013.01); *C09K 2211/1466* (2013.01)

(58) Field of Classification Search
CPC . C09K 11/06; C09K 11/02; C09K 2211/1033; C09K 2211/1088; C09K 2211/1096; C09K 2211/1029; C09K 2211/1466; B82Y 30/00; C09B 67/0013; C09B 67/0097; C09B 11/24; C09B 19/00; C09B 29/08
See application file for complete search history.

(56) References Cited

U.S. PATENT DOCUMENTS

| 2016/0018300 A1* | 1/2016 | Takanashi | ............... | C09B 68/41 435/40.5 |
| 2018/0011086 A1* | 1/2018 | Isoda | ..................... | G01N 33/48 |

FOREIGN PATENT DOCUMENTS

| EP | 2613138 A1 | 7/2013 |
|---|---|---|
| JP | 2008-543982 A | 12/2008 |
| JP | 2015-108572 | 6/2015 |
| WO | 2012029752 A1 | 3/2012 |
| WO | 2013035703 A1 | 3/2013 |
| WO | 2014136776 A1 | 9/2014 |
| WO | 2014136885 A1 | 9/2014 |
| WO | WO 2014/136885 * | 9/2014 |
| WO | 2014203614 A1 | 12/2014 |

(Continued)

OTHER PUBLICATIONS

JPO, Office Action for the corresponding Japanese patent application No. 2017-555992, dated Dec. 3, 2019, with English translation (8 pages).
International Search Report dated Feb. 21, 2017 from corresponding International Application No. PCT/JP2016/086144 and English translation.

(Continued)

*Primary Examiner* — C Melissa Koslow
(74) *Attorney, Agent, or Firm* — Lucas & Mercanti, LLP

(57) ABSTRACT

The present invention provides a nanoparticle containing a hydrophobic fluorescent substance accumulated therein and a thermosetting resin as a matrix, which nanoparticle, when used for labeling of a biological substance such as a protein or nucleic acid, has brightness sufficient for allowing pathological diagnosis using a fluorescence image obtained thereby. The present invention is a phosphor integrated dots nanoparticles wherein a thermosetting resin contains a structural unit formed from a raw material containing a hydrophobic substituent, and wherein a fluorescent substance is accumulated in the nanoparticle at least by hydrophobic interaction, preferably further by stacking interaction, with the hydrophobic substituent of the thermosetting resin.

9 Claims, No Drawings

(56) References Cited

FOREIGN PATENT DOCUMENTS

| WO | 2015141856 A1 | | 9/2015 |
|---|---|---|---|
| WO | 2016117054 A1 | | 7/2016 |
| WO | WO 2016/117054 | * | 7/2016 |

OTHER PUBLICATIONS

Written Opinion of the International Searching Authority dated Feb. 21, 2017 from corresponding International Application No. PCT/JP2016/086144 and English translation.
Extended European Search Report dated Mar. 21, 2019 issued in connection with corresponding European patent application No. 16875459.6.

* cited by examiner

PHOSPHOR INTEGRATED DOTS NANOPARTICLES AND LABELING AGENT USING SAME

CROSS REFERENCE TO RELATED APPLICATION

This Application is a 371 of PCT/JP2016/086144 filed on Dec. 6, 2016 which, in turn, claimed the priority of Japanese Patent Application No. JP 2015-247590 filed on Dec. 18, 2015, both applications are incorporated herein by reference.

TECHNICAL FIELD

The present invention relates to phosphor integrated dots nanoparticles and a labeling agent using it. More specifically, the present invention relates to phosphor integrated dots nanoparticles using a thermosetting resin as a matrix, and a labeling agent using it.

BACKGROUND ART

Medical diagnosis includes pathological diagnosis. In pathological diagnosis, a pathological specimen prepared from a sample tissues collected from a human body is observed by a pathologist to diagnose a disease, and judgment on necessity of a treatment or surgery is reported to the clinician. Based on conditions of the patient and the pathological diagnosis, a physician in the field of internal medicine determines the course of medication, and a physician in the field of surgery determines whether a surgical operation is to be carried out or not.

In pathological diagnosis of cancer/malignant tumor, the morphology of a tissue or cells in a pathological specimen is observed, and in some cases, the expression level of a particular protein contained in the specimen or the copy number of a particular gene in a chromosome is examined. Examples of pathological diagnoses widely carried out include those in which the HER2 gene (HER2/neu, c-erbB-2) and/or HER2 protein, which is a membrane protein produced from the HER2 gene and assumed to function as a receptor of a cancer cell growth factor, is/are quantified and evaluated according to a predetermined standard to perform prognostic diagnosis of a breast cancer patient, and those in which therapeutic effects of a molecular-targeted therapeutic agent "trastuzumab" (trade name "Herceptin" (registered trademark), anti-HER2 monoclonal antibody) are predicted.

A representative test method for such a protein is the IHC (immunohistochemistry) method, and a representative test method for the gene is the FISH (fluorescence in situ hybridization) method. Detection by the IHC method has been commonly carried out by a method in which an enzymatically labeled antibody is bound to a protein (antigen) of interest by a direct method or an indirect method, and then a substrate is reacted therewith to cause coloring (for example, DAB staining using peroxidase and diaminobenzidine), that is, the so-called immunostaining. In detection by the FISH method, a fluorescently labeled nucleic acid probe is hybridized with a gene of interest. This has been conventionally commonly carried out by linking a plurality of fluorescent dye molecules to the nucleic acid probe to perform fluorescent labeling.

However, enzymatic staining such as DAB staining in the IHC method has a problem in that, since the staining density largely varies depending on environmental conditions such as the temperature and the time, the actual amount of antigen or the like cannot be easily estimated based on the staining density. Further, staining using a fluorescent dye molecule in the FISH method has a problem in that, since brightness of the fluorescence is relatively low, observation and imaging under a fluorescence microscope results in poor visibility, and that discoloration quickly occurs.

Under such circumstances, for labeling of a gene or protein in pathological diagnosis, methods using a nano-sized particle in which a fluorescent substance (fluorescent dye, quantum dot, or the like) is accumulated, that is, phosphor integrated dots nanoparticles, have recently been proposed, and their practical application is in progress. By labeling a protein or gene using phosphor integrated dots nanoparticles, and radiating an excitation light suitable for the fluorescent substance, the phosphor integrated dots nanoparticles can be observed as a bright spot having high brightness that correctly indicates the position of the protein or gene. The method is also advantageous in that, since discoloration of the fluorescence is less likely to occur, observation and imaging are possible for a relatively long time. For example, WO 2012/029752 (Patent Document 1) and WO 2013/035703 (Patent Document 2), describe methods in which immunostaining is carried out using an antibody to which phosphor integrated dots nanoparticles are linked. WO 2015/141856 (Patent Document 3) describes carrying out of the FISH method using a nucleic acid probe to which phosphor integrated dots nanoparticles is linked.

Regarding such phosphor integrated dots nanoparticles, development of phosphor integrated dots nanoparticles with higher performances has been attempted focusing on the fluorescent substance to be accumulated and the material (silica, thermosetting resin, thermoplastic resin, or the like) of the matrix in which such a fluorescent substance is to be accumulated to form a particle.

For example, Japanese Translated PCT Patent Application Laid-open No. 2008-543982 (Patent Document 4) describes use of a particular production method to obtain a melamine/formaldehyde particle having a particle size of 10 to 95 nm wherein an organic fluorescent dye or the like is encapsulated. The document describes, as examples of the fluorescent dye, hydrophilic organic fluorescent dyes such as rhodamine-based, fluorescein-based, and coumarin-based organic fluorescent dyes; and trisodium 8-hydroxy-1,3,6-pyrenetrisulfonate.

WO 2014/136885 (Patent Document 5) discloses a nanoparticle containing a thermosetting resin as a matrix and a fluorescent dye accumulated thereto, wherein the thermosetting resin and the fluorescent dye have substituents having charges opposite to each other, and wherein these substituents are bound to each other by ionic bonding or covalent bonding (and wherein the particle size change coefficient is not more than 15%). The document describes, as an example of the thermosetting resin, a melamine resin containing a positively charged amino group (or a moiety similar thereto), and, as an example of the fluorescent dye, a rhodamine-based or aromatic hydrocarbon-based dye molecule containing a negatively charged sulfo group. The document describes that such a fluorescent dye-accumulated nanoparticle allows suppression of variability of the intensity of the bright spot and prevention of bleeding of the fluorescent dye from the nanoparticle, thereby enabling improvement of the accuracy of evaluation of the fluorescence signals.

Patent Document 5 describes, for example, that "in cases where the fluorescent dye is a rhodamine-, BODIPY-, squarylium-, or aromatic hydrocarbon-based dye molecule, interaction between hydrophobic moieties of the fluorescent dye and the resin, together with ionic bonding between substituents, enables strong binding between the dye molecule and the resin" and that "in cases where the thermosetting resin is formed using melamine, and the fluorescent dye is a rhodamine- or aromatic hydrocarbon-based dye molecule, hydrophobic interaction between benzene rings contained in the melamine resin and the rhodamine- or aromatic hydrocarbon-based dye molecule, together with the above-described ionic bonding between substituents, enables stronger binding between the dye molecule and the resin" (see paragraphs [0101] and [0102]). However, in cases where the particular fluorescent dye described above is uncharged, its accumulation using a melamine resin prepared by homopolymerization of methyl etherified methylol melamine (NIKALAC MX-035) (see Example 1, cited in Comparative Example 40 and the like), a urea resin prepared by homopolymerization of urea with a methylolation rate of 40 to 70% (see Example 2, cited in Comparative Example 41 and the like), or a copolymer of their monomers with a xylene resin (NIKANOL Y-50) or the like (see Example 3, cited in Comparative Example 42 and the like) has been unsuccessful, and the resulting nanoparticle could not be observed as a bright spot having sufficient brightness when it was used in immunostaining (Comparative Examples 40 to 51, paragraph [0160] Table 1). That is, Patent Document 5 does not specifically disclose that a thermosetting resin nanoparticle in which a hydrophobic fluorescent dye is accumulated can be produced by hydrophobic interaction alone in cases where the thermosetting resin and the fluorescent dye do not have substituents having charges opposite to each other.

DOCUMENTS OF RELATED ART

Patent Documents

[Patent Document 1] WO 2012/029752
[Patent Document 2] WO 2013/035703
[Patent Document 3] WO 2015/141856
[Patent Document 4] JP2008-543982A
[Patent Document 5] WO 2014/136885

SUMMARY OF THE INVENTION

Problems to be Solved by the Invention

A variety of compounds are known as fluorescent dyes, and not a small number of fluorescent dyes having high hydrophobicity show excellent fluorescence properties. However, because of such high hydrophobicity, such fluorescent dyes cannot be easily used alone (without accumulation) for labeling of a biological molecule such as a protein or nucleic acid in an immunostaining method or FISH method, in which treatment is carried out mainly using an aqueous solution. When preparation of phosphor integrated dots nanoparticles was attempted using a highly hydrophobic fluorescent dye and a thermosetting resin excellent in the luminescence intensity, light resistance, solvent resistance, and the like, for example, a melamine resin synthesized by homopolymerization of methyl alkylated methylol melamine (a compound prepared by substituting, with a methyl group, the hydrogen atom of the hydroxyl group of methylol melamine, which is a compound formed by binding formaldehyde to an amino group of melamine; —NH—CH$_2$—O—CH$_3$), accumulation of the fluorescent dye in the particle was difficult due to the high hydrophobicity, resulting in production of a particle showing very low brightness which is impractical for pathological diagnosis. In Patent Documents 4 and 5, any of the thermosetting resin nanoparticles specifically disclosed as preferred thermosetting resin nanoparticles in Examples is a thermosetting resin nanoparticle in which a water-soluble fluorescent dye is accumulated or a thermosetting resin nanoparticle prepared by binding a fluorescent dye to a thermosetting resin by ionic bonding or covalent bonding utilizing charged substituents.

As fluorescent substances other than fluorescent dyes, "quantum dots" (for example, microparticles composed of a semiconductor ZnSe) are widely known, and phosphor integrated dots nanoparticles in which quantum dots are accumulated using silica as a matrix have been produced (see, for example, Patent Document 1). However, some quantum dots such as CdSe have a hydrophobic surface, and are stored in the state of a dispersion in an organic solvent (such as decane). Although the surface of such hydrophobic quantum dots can be hydrophilized by modification using a silane coupling agent and a hydrophilic macromolecule such as polyethylene glycol (PEG), such modification often results in a lower luminescence intensity compared to the unmodified (that is, hydrophobic) state. Phosphor integrated dots nanoparticles in which a hydrophobic quantum dot is accumulated using as a matrix a thermosetting resin such as a melamine resin having better light resistance than silica has not been obtained yet.

The present invention was made in view of the above problems, and aims to provide a thermosetting resin nanoparticle in which a highly hydrophobic fluorescent substance is accumulated, which nanoparticle, when used for labeling of a biological substance such as a protein or nucleic acid, has a brightness sufficient for allowing pathological diagnosis using a fluorescence image obtained therewith.

Means for Solving the Problems

The inventors discovered that, by using as a matrix a thermosetting resin synthesized using a raw material containing a hydrophobic substituent (functional group), for example, a melamine resin synthesized by polymerization of a butylated melamine resin (a resin prepared by substituting the methyl group of a methylated melamine resin with a butyl group; —NH—CH$_2$—O—C$_4$H$_9$) instead of the methylated melamine resin described above, a highly hydrophobic fluorescent substance can be accumulated to allow production of phosphor integrated dots nanoparticles with excellent performance, thereby completing the present invention.

That is, the phosphor integrated dots nanoparticles according to the present invention are nanoparticles comprising a hydrophobic fluorescent substance accumulated therein and a thermosetting resin as a matrix, the thermosetting resin containing a structural unit formed from a raw material containing a hydrophobic substituent, the hydrophobic fluorescent substance being accumulated in the nanoparticle at least by hydrophobic interaction with the hydrophobic substituent of the thermosetting resin.

The labeling agent according to the present invention comprises the phosphor integrated dots nanoparticles according to the present invention and a substance linked to the surface thereof which specifically binds to a biologically relevant substance of interest (that is, the labeling agent is a conjugate).

Effect of the Invention

The present invention enables preparation of phosphor integrated dots nanoparticles using a highly hydrophobic fluorescent substance of which utilization of properties such as high luminescence intensity has been insufficient, and use of the phosphor integrated dots nanoparticles. Thus, pathological diagnosis with improved reliability may become possible by use of a fluorescence image showing excellent qualities in visibility (brightness, color tone, and the like).

DETAILED DESCRIPTION OF THE INVENTION

—Phosphor Integrated Dots Nanoparticles—

The phosphor integrated dots nanoparticles of the present invention are nanoparticles comprising a hydrophobic fluorescent substance accumulated therein and a thermosetting resin as a matrix, the thermosetting resin containing a structural unit formed from a raw material containing a hydrophobic substituent, the hydrophobic fluorescent substance being accumulated in the nanoparticle at least by hydrophobic interaction with the hydrophobic substituent of the thermosetting resin.

"Raw material" includes the monomers used for synthesis of the thermosetting resin, as well as compounds (prepolymers and resin intermediates) obtained by preliminarily partially reacting the monomers with a cross-linking agent (formaldehyde), such as methylol melamine and methylol xylene which may be alkyl etherified, and other compounds that are used depending on the synthetic reaction of the thermosetting resin. Such materials other than the monomers correspond to "derivatives" of the monomers.

"Hydrophobic fluorescent substance being accumulated in the nanoparticle at least by hydrophobic interaction with the hydrophobic substituent of the thermosetting resin" can be assumed, as described in the later-mentioned Examples, based on the fact that, when a nanoparticle is prepared using a hydrophobic fluorescent substance and a thermosetting resin containing a hydrophobic substituent, the brightness of the fluorescence of the generated nanoparticle is, for example, not less than 10-fold, preferably not less than 100-fold enhanced compared to a case where a nanoparticle is prepared using the hydrophobic fluorescent substance and a thermosetting resin containing no hydrophobic substituent. In general, in the production process of phosphor integrated dots nanoparticles, the raw material of the thermosetting resin and the hydrophobic fluorescent substance are mixed together in an aqueous solution. It is thought that, since a large amount of the hydrophobic fluorescent substance tends to accumulate in the inside (the side not contacting with water) of the thermosetting resin due to hydrophobic interaction, such an enhancing effect on the fluorescence brightness can be achieved. Further, it is thought that, after the production of the phosphor integrated dots nanoparticles, release of the fluorescent substance from the nanoparticle can be suppressed in the aqueous solution (dispersion), and degradation of the fluorescent substance (fluorescent dye) can be suppressed by preventing infiltration of water into the particle.

Although at least hydrophobic interaction is acting between the hydrophobic fluorescent substance and the hydrophobic substituent of the thermosetting resin, this does not mean elimination of other additional noncovalent interactions (excluding ionic bonding).

Examples of the interactions other than hydrophobic interaction include stacking interaction ($\pi$-$\pi$ interaction) that acts between aromatic rings. As will be described later in detail, in cases where the thermosetting resin contains as a hydrophobic substituent an aromatic ring such as an aryl group or heteroaryl group, and the fluorescent substance is a fluorescent dye containing such an aromatic ring, or containing an aromatic ring in the major part (basic skeleton) of the molecular structure, stacking interaction acts between those aromatic rings. It is thought that the resulting stronger interaction between the thermosetting resin and the fluorescent substance enables further enhancement of the action and the effect of the present invention described above, allowing maintenance of a strong fluorescence intensity for a long time.

The particle size of the phosphor integrated dots nanoparticles can be adjusted to an appropriate range depending on the use. For example, in cases where the nanoparticle is used for preparation of a labeling agent for staining a biological substance in a tissue section, the average particle size is usually 10 to 500 nm, preferably 50 to 200 nm. The coefficient of variation (CV), which represents variation of the particle size, is usually not more than 20%, preferably 5 to 15%. Phosphor integrated dots nanoparticles having such a particle size can be obtained by, for example, the production method described later.

The particle size of the phosphor integrated dots nanoparticles can be measured by taking an electron micrograph using a scanning electron microscope (SEM) and measuring the cross-sectional area of the resin particle for fluorescent labeling, followed by assuming a circle having the same area as the measured area and calculating the diameter of this circle (area equivalent circle diameter). The average particle size and the coefficient of variation of a population of phosphor integrated dots nanoparticles can be calculated by measuring the particle sizes of a sufficient number of (for example, 300) phosphor integrated dots nanoparticles as described above, calculating their arithmetic average to determine the average particle size, and then calculating the coefficient of variation according to the following equation: 100×standard deviation of the particle size/average particle size.

(Fluorescent Substance)

The "fluorescent substance" constituting the phosphor integrated dots nanoparticles of the present invention is not limited as long as it is hydrophobic and can be accumulated in a nanoparticle upon its formation by a thermosetting resin containing a hydrophobic substituent. Since the present invention is essentially different from an invention aiming at production of an action and an effect by utilizing ionic bonding between a positive or negative charge of a substituent or another moiety in a fluorescent dye or the like and the opposite charge of a substituent or another moiety in a thermosetting resin, or by utilizing covalent bonding (see WO 2014/136885; Patent Document 5), the fluorescent substance used in the present invention may be limited, if necessary, to a fluorescent substance which contains neither a substituent (for example, a carboxyl group, sulfo group, or amino group) or a moiety similar thereto charged to a strength sufficient for causing ionic bonding to a certain site of a thermosetting resin, nor a substituent or another moiety that causes covalent bonding to a certain site of a thermosetting resin.

Representative examples of the hydrophobic fluorescent substance include fluorescent dyes and quantum dots formed from hydrophobic compounds (semiconductors). Common types of hydrophobic (lipophilic) fluorescent substances are handled after being dissolved or dispersed in an organic solvent rather than water.

Examples of fluorescent dyes include rhodamine-based dye molecules, squarylium-based dye molecules, cyanine-based dye molecules, perylene-based (perylene diimide-based) dye molecules, pyrene-based dye molecules, oxazine-based (benzophenoxazine-based) dye molecules, azobenzene-based (azonaphthalene-based) dye molecules, carbopyronine-based dye molecules, pyrromethene-based dye molecules, Alexa Fluor (registered trademark, manufactured by Invitrogen)-based dye molecules, BODIPY (registered trademark, manufactured by Invitrogen)-based dye molecules, Cy (registered trademark, manufactured by GE Healthcare)-based dye molecules, DY-based dye molecules (registered trademark, manufactured by DYOMICS), HiLyte (registered trademark, manufactured by AnaSpec, Inc.)-based dye molecules, DyLight (registered trademark, manufactured by Thermo Scientific)-based dye molecules, ATTO (registered trademark, manufactured by ATTO-TEC)-based dye molecules, MFP (registered trademark, manufactured by Mobitec)-based dye molecules, and FM-based dye molecules.

In the present invention, hydrophobic or lipophilic fluorescent dyes among such known fluorescent dyes, for example, hydrophobic fluorescent dyes among rhodamine-based dye molecules, squarylium-based dye molecules, pyrene-based dye molecules, perylene diimide-based dye molecules, benzophenoxazine-based dye molecules, BODIPY-based dye molecules, and FM-based dye molecules; and benzophenoxazine-based dye molecules, which are used as staining agents for hydrophobic portions (lipid and the like) of cells and tissues; may be used as the hydrophobic fluorescent substance to be accumulated in the resin nanoparticle. Specific examples of such fluorescent dyes include BODIPY-based dye molecules including BODIPY 493/503, BODIPY FL, BODIPY R6G, BODIPY TMR, BODIPY 581/591, BODIPY TR, BODIPY 630/650, and BODIPY 650/665; FM-based dye molecules including FM 1-43, FM 1-43FX, FM 4-64, and FM 4-64FX; oxazine-based (benzophenoxazine-based) dye molecules including Nile Red and Nile Blue; and azobenzene-based (azonaphthalene-based) dye molecules including Oil Red. Each of these fluorescent dyes contains an aromatic ring in the major part (basic skeleton) of its molecular structure, and is therefore likely to be a highly hydrophobic fluorescent dye (see the Formulae (1) to (8) shown below). The fluorescent dye may also contain a hydrophobic substituent described for the thermosetting resin. In cases where two or more hydrophobic substituents are contained per one fluorescent dye molecule, hydrophobic interaction with the hydrophobic substituent contained in the thermosetting resin occurs in a larger number of moieties, so that the interaction becomes stable and strong, which is preferred.

Basic Skeletons of Fluorescent Dyes

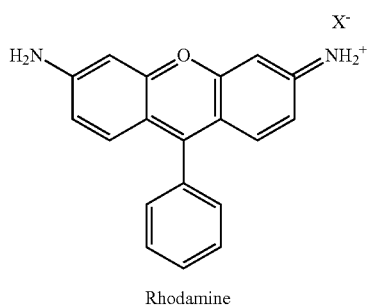

Rhodamine (2)

Squarylium (3)

Pyrene (4)

Perylene diimide (5)

Benzophnoxazine (6)

Azobnzene-azonaphthalene (7)

BODIPY (8)

FM

Examples of quantum dots include II-VI group semiconductor quantum dots, III-V group semiconductor quantum dots, IV group semiconductor quantum dots, and semiconductor quantum dots having a core-shell structure in which the surface of these semiconductor quantum dots is coated with another semiconductor having a wider band gap. In the present invention, among such known quantum dots, hydrophobic quantum dots such as CdSe, which is a II-VI group semiconductor quantum dot, and CdSe/ZnS, which is a core-shell structure thereof, may be used as the hydrophobic fluorescent substance to be accumulated in the nanoparticle. In general, a quantum dot prepared by an organic solution method becomes a hydrophobic quantum dot due to attachment of a hydrophobic ligand to the surface.

(Thermosetting Resin)

The resin constituting the phosphor integrated dots nanoparticles of the present invention is not limited as long as it is a thermosetting resin containing structural units formed from a raw material(s) containing a hydrophobic substituent, and as long as a hydrophobic fluorescent substance can be accumulated in the resin nanoparticle by hydrophobic interaction between the hydrophobic substituent and the hydrophobic fluorescent substance.

The structural units formed from the raw material(s) of the thermosetting resin may be entirely structural units (a) formed from a raw material(s) containing a hydrophobic substituent, or may include both structural units (a) formed from a raw material(s) containing a hydrophobic substituent and structural units (b) formed from a raw material(s) containing no hydrophobic substituent. The ratio between the structural units (a) and (b) may be appropriately controlled taking into account properties such as the strength of hydrophobicity of each raw material and the effect of hydrophobic interaction on accumulation of the hydrophobic fluorescent substance, that is, the brightness (luminescence intensity) of the fluorescent substance-accumulated resin particle obtained. For example, the weight ratio between the raw materials of the structural units (a) and (b) may be (a):(b)=30:70 to 80:20, preferably 40:60 to 70:30. In cases where the weight ratio of the material(s) containing a hydrophobic substituent for the structural units (a) is too small, the effect to allow accumulation of the hydrophobic fluorescent substance may not be produced, while in cases where the weight ratio is too large, the surface of the phosphor integrated dots nanoparticles becomes too hydrophobic, so that aggregation of the particles is likely to occur in the dispersion medium (buffer or the like).

In cases where the structural units formed from the raw material(s) of the thermosetting resin are entirely structural units (a) formed from a raw material(s) containing a hydrophobic substituent, or in cases where the structural units formed from the raw material(s) of the thermosetting resin include both structural units (a) formed from a raw material(s) containing a hydrophobic substituent and structural units (b) formed from a raw material(s) containing no hydrophobic substituent, and the ratio (raw material weight ratio) of the former structural units is relatively large, it is preferred to perform treatment to hydrophilize the surface of the phosphor integrated dots nanoparticles in order to prevent aggregation in the dispersion medium. This hydrophilization treatment will be described later.

The type and the degree of hydrophobicity of the hydrophobic substituent contained in the thermosetting resin are not limited, and may be selected from substituents known to have hydrophobic properties, taking into account properties of the hydrophobic fluorescent substance to be used in combination therewith, and the like. In general, the hydrophobic substituent may be, for example, an alkyl group, alkenyl group, alkynyl group, aryl group, or heteroaryl group. For example, the hydrophobic substituent in the present invention is preferably at least one selected from the group consisting of $C_4$-$C_{10}$ linear, branched, or cyclic alkyl groups, alkenyl groups, and alkynyl groups each of which optionally has a substituent(s); and $C_6$-$C_{15}$ aryl groups and heteroaryl groups each of which optionally has a substituent(s). Among these, aryl groups, especially a phenyl group, is more preferred since they can produce stronger and more stable hydrophobic interaction.

The thermosetting resin that may be used in the present invention is preferably a thermosetting resin containing a structural unit(s) formed from one or more raw materials which are selected from the group consisting of, for example, melamine, guanamine, aniline, urea, phenol, xylene, and derivatives thereof, and which include a raw material containing a hydrophobic substituent. The thermosetting resin, in other words, can be produced using one or more raw materials which are selected from the group consisting of melamine, guanamine, aniline, urea, phenol, xylene, and derivatives thereof, and which include a raw material containing a hydrophobic substituent. Any of melamine, guanamine, aniline, urea, phenol, xylene, and derivatives thereof reacts with an aldehyde such as formaldehyde to undergo addition polymerization. Any one of these raw materials may be used alone, or two or more of these may be used in combination. That is, the thermosetting resin may be a homopolymer containing structural units formed from any one of the raw materials, or may be a copolymer containing structural units formed from two or more raw materials. The raw material(s) for production of the thermosetting resin may be entirely a raw material(s) selected from the particular group described above, or may be a mixture of a raw material(s) selected from the particular group described above and another raw material(s).

The thermosetting resin in the present invention is more preferably a thermosetting resin containing (or composed of) a structural unit(s) formed from at least one raw material selected from the group consisting of melamine, guanamine, and derivatives thereof, that is, a melamine resin, guanamine resin, or melamine/guanamine copolymer. Among melamine, guanamine, and derivatives thereof, examples of raw materials containing a hydrophobic substituent include butyl etherified methylol melamine, benzoguanamine, butyl etherified methylol guanamine, and butyl etherified methylol benzoguanamine (see the Formulae (9) to (12) shown below; in Formulae (9) to (12), the R's each independently represent H, —CH$_2$OH, or —CH$_2$OR' (with the proviso that at least one of these represents —CH$_2$OR'), wherein R' represents a hydrophobic substituent such as a butyl group).

Examples of Thermosetting Resin Raw Materials Containing a Hydrophobic Substituent

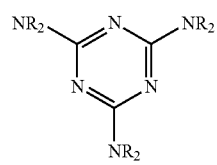

Alkyl etherified
methylol melamine

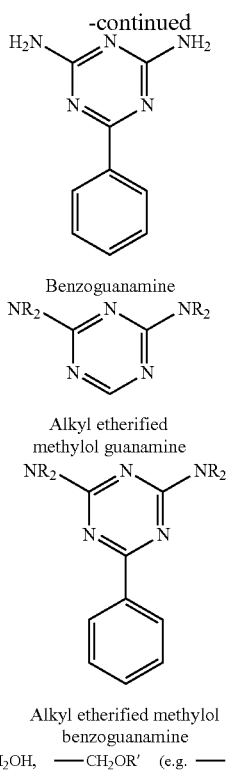

Benzoguanamine

Alkyl etherified methylol guanamine

Alkyl etherified methylol benzoguanamine

R: —H, —CH₂OH, —CH₂OR' (e.g. —CH₂OBu)

Melamine (1,3,5-triazine-2,4,6-triamine) is a compound in which three amino groups (—NH₂) are bound to a triazine ring (C₃N₃H₆), and polycondensation reaction products of melamine and formaldehyde thermosetting resins that are well known as melamine resins. In reaction of melamine with formaldehyde, addition of formaldehyde to an amino group of one melamine first occurs to cause methylolation (—NH—CH₂OH), and then an amino group of another melamine reacts therewith to cause methylenation (—NH—CH₂—NH—) by dehydration condensation, resulting in formation of a three-dimensional network structure by cross-linking between the amino groups of the melamines through formaldehyde (methylene group), to produce a thermosetting resin. In general, a melamine resin is synthesized by preliminarily preparing a compound in which a part or all of the amino groups of melamine are methylolated by reaction with formaldehyde, that is, a methylol melamine in which one to six hydrogen atoms out of the total of six hydrogen atoms contained in the three amino groups are substituted by a methylol group(s), and then heating this compound to allow polycondensation. Since methylol has low stability in water, an alkyl etherified methylol melamine prepared by etherifying a methylol group of methylol melamine with an alcohol such as methanol or butanol (—NH—CH₂O—R, wherein R represents an alkyl group such as a methyl group or butyl group) is also used as a raw material in the synthetic method for a melamine resin described above (for trade names, alkyl etherified methylol melamine is abbreviated as, for example, "methylated melamine" in cases where the alkyl group is a methyl group, or "butylated melamine" in cases where the alkyl group is a butyl group). Methyl ether methylol melamine, which is produced by etherification with methanol, is water-soluble, and easily dissolves in water. In contrast, butyl ether methylol melamine, which is produced by etherification with butanol, is hydrophobic (lipophilic), and easily dissolves in an organic solvent.

In the present invention, the alkyl group introduced in an alkyl etherified methylol melamine can be the hydrophobic substituent that should be contained in the thermosetting resin. For example, in cases where a melamine resin is synthesized using a butyl etherified methylol melamine in which a plurality of butyl groups, which are C₄ alkyl groups, are introduced, a part of the butyl etherified methylol groups remain unreacted in the melamine resin. Thus, a melamine resin containing a butyl group as a hydrophobic substituent is obtained.

Guanamine (1,3,5-triazine-2,4-diamine) is a compound in which two amino groups are bound to a triazine ring, and 6-substituted guanamines, in which a substituent such as an alkyl group or a phenyl group is introduced to the 6-position of a triazine ring (for example, benzoguanamine, which is substituted with a phenyl group), are also known. Similarly to melamine, guanamine and its derivatives (including 6-substituted guanamines) form guanamine resins by polycondensation with formaldehyde. As raw materials of guanamine resins, alkyl etherified methylol guanamines are also used.

In the present invention, guanamine or 6-substituted guanamines may be used similarly to melamine—the alkyl group introduced in an alkyl etherified methylol guanamine or alkyl etherified methylol 6-substituted guanamine can be the hydrophobic substituent that should be contained in the thermosetting resin. Further, among 6-substituted guanamines, in compounds such as benzoguanamine that are substituted by a hydrophobic substituent (phenyl group, in this case), this hydrophobic substituent (substituent) can also be the hydrophobic substituent that should be contained in the thermosetting resin. The raw material of the thermosetting resin may be a material having two or more hydrophobic substituents per one molecule, for example, butyl etherified methylol benzoguanamine.

The raw material of the thermosetting resin of the present invention may also be a raw material such as phenol, xylene, aniline, or a derivative thereof in which a benzene ring has a predetermined substituent(s) (—OH in the case of phenol, two —CH₃'s in the case of xylene, and —NH₂ in the case of aniline) and optionally another substituent(s). The benzene ring contained in each of these raw materials can also be the hydrophobic substituent that should be contained in the thermosetting resin. Regarding derivatives in which a hydrophobic substituent such as an alkyl group or aryl group is introduced as another substituent, this substituent can also be the hydrophobic substituent that should be contained in the thermosetting resin.

(Method for Producing Phosphor Integrated Dots Nanoparticles)

From the viewpoint of the fact that the fluorescent substance to be accumulated is hydrophobic, the phosphor integrated dots nanoparticles of the present invention are rather different from conventional phosphor integrated dots nanoparticles, in which the fluorescent substance to be accumulated is hydrophilic in most cases. However, the phosphor integrated dots nanoparticles of the present invention can be produced basically by the same method as in the cases of conventional phosphor integrated dots nanoparticles using a thermosetting resin as a matrix, typically by the emulsion polymerization method.

Basically, for example, in cases where a melamine resin is used as the thermosetting resin, a hydrophobic fluorescent substance, a raw material(s) of the melamine resin (for example, methylol melamine in a powder form), and, if necessary, other additives and the like are mixed together, and the resulting mixture is heated to allow polymerization reaction to proceed. As the polymerization reaction of the melamine resin proceeds, particles are formed, and the hydrophobic fluorescent substance is incorporated and accumulated into the particles. In the present invention, the raw material(s) of the melamine resin need(s) to include at least one raw material containing a hydrophobic substituent. In cases where two or more raw materials are used in combination, their ratios (molar ratios) in the raw materials correspond to the ratios (molar ratios) of the structural units formed from the respective raw materials in the thermosetting resin produced.

The conditions (temperature, time, and the like) of the polymerization reaction may be appropriately set taking into account the type of the resin, the composition of the raw material(s), and the like. In the synthesis of the thermosetting resin such as a melamine resin, the reaction temperature is usually 70 to 200° C., and the reaction time is usually 20 to 120 minutes. The reaction temperature is appropriately set to a temperature at which the performance of the fluorescent substance, especially the fluorescent dye, is not deteriorated (within the heat-resistant temperature range). The heating may be carried out in a plurality of steps. For example, the reaction may be allowed to proceed at a relatively low temperature for a certain length of time, and then the temperature may be increased, followed by allowing the reaction to proceed at a relatively high temperature for a certain length of time. The heat-resistant temperature of the fluorescent dye is about 200° C. in the cases of rhodamine-based dye molecules, BODIPY (registered trademark, manufactured by Invitrogen)-based dye molecules, squarylium-based dye molecules, and the like, and not less than about 300° C. in cases of pyrene-based dye molecules, perylene-based dye molecules, and the like.

After completion of the polymerization reaction, impurities such as the residual resin material, fluorescent dye, and other additives (the supernatant containing these) may be removed by centrifugation or the like from the resulting dispersion of phosphor integrated dots nanoparticles, and then the phosphor integrated dots nanoparticles (the precipitate) may be collected, followed by washing the nanoparticles. The removal of the impurities may be carried out by operations such as centrifugation, and the washing of the phosphor integrated dots nanoparticles may be carried out by operations such as ultrasonic irradiation and redispersion in ultrapure water. A series of washing operations such as the centrifugation, removal of the supernatant, and redispersion in ultrapure water may be appropriately repeated a plurality of times until disappearance of the absorbance and/or fluorescence derived from the fluorescent substance and the thermosetting resin in the supernatant of the redispersion liquid of the phosphor integrated dots nanoparticles.

Also in cases where another thermosetting resin is used, the phosphor integrated dots nanoparticles may be produced by the same method as in the cases where the melamine resin is used, or by another known method (see, for example, WO 2014/136885; Patent Document 5), using a different raw material(s) and reaction conditions as required.

(Hydrophilization Treatment)

In cases where the surface of the phosphor integrated dots nanoparticles is to be hydrophilized as described above after the polymerization step of the thermosetting resin, a hydrophilization treatment may be carried out therefor. The hydrophilization treatment of the surface of the phosphor integrated dots nanoparticles may be carried out by a known method. It is preferred to link a hydrophilic macromolecule such as polyethylene glycol (PEG) to the surface of the phosphor integrated dots nanoparticles using a silane coupling agent.

For example, synthesis of a melamine resin, which is a representative thermosetting resin to be used in the present invention, is carried out using a methylol melamine wherein a methylol group(s) (—CH$_2$OH), and/or a substituted methylol group(s) (—CH$_2$OR) having an alkyl group such as a methyl group introduced thereto as a hydrophobic substituent, is/are bound to an amino group(s). After the synthesis reaction, the hydroxyl group(s) (—OH) contained in the methylol group(s) and/or the hydroxyl group(s) generated from the substituted methylol group(s) in such a methylol melamine is/are exposed on the surface of the phosphor integrated dots nanoparticles. Here, a silane coupling agent containing an alkoxy group and a functional group such as an amino group can bind to a hydroxyl group of the melamine resin through the alkoxy group, and at the same time, can bind, through the functional group such as an amino group, to a PEG in which a functional group reactive with an amino group, for example, an NHS (N-hydroxysuccinimide) group, is preliminarily introduced to its terminus. Thus, by reacting a silane coupling agent with the phosphor integrated dots nanoparticles containing a melamine resin as a matrix, and then reacting a predetermined PEG containing an NHS group introduced thereto with the reaction product, the surface of the phosphor integrated dots nanoparticles can be modified with the PEG to impart hydrophilicity. The combination of the functional group contained in the thermosetting resin and the alkoxy group contained in the silane coupling agent, and the combination of the functional group contained in the silane coupling agent and the functional group introduced to the hydrophilic macromolecule are not limited to those exemplified above. Various combinations may be employed as long as appropriate reactions can be allowed to occur.

As described below, in preparation of a labeling agent using the phosphor integrated dots nanoparticles, when the surface of the phosphor integrated dots nanoparticles is treated using a linker (wherein a functional group reactive with a silane coupling agent is introduced to one end, and a functional group reactive with a functional group contained in a biologically relevant binding substance is introduced to the other end) containing a hydrophilic macromolecule such as a PEG for linking the phosphor integrated dots nanoparticles to a biologically relevant binding substance (antibody or the like), the surface of the phosphor integrated dots nanoparticles can be hydrophilized by this treatment.

(Use of Phosphor Integrated Dots Nanoparticles)

The use of the phosphor integrated dots nanoparticles of the present invention is not limited, and a variety of uses can be assumed similarly to the known phosphor integrated dots nanoparticles. Typically, the phosphor integrated dots nanoparticles of the present invention may be used for preparation of labeling agents such as those described below.

—Labeling Agent—

The labeling agent of the present invention comprises the phosphor integrated dots nanoparticles of the present invention and a biologically relevant binding substance linked to the surface thereof. In the present invention, although a hydrophobic fluorescent substance is accumulated in a nanoparticle containing a thermosetting resin as a matrix, the preparation method and the use of the labeling agent are basically the same as those of known labeling agents. For more detailed matters and specific embodiments, one may refer to the later-mentioned Examples in the present description, and, for example, WO 2012/029752 (Patent Document 1), WO 2013/035703 (Patent Document 2), and WO 2014/136885 (Patent Document 5), which mainly describe labeling agents used in immunostaining, as well as WO 2015/141856 (Patent Document 3), which mainly describes labeling agents used in the FISH method.

(Biologically Relevant Binding Substance)

As the biologically relevant binding substance, a variety of substances can be used depending on the use of the labeling agent, that is, how the labeling agent is directly or indirectly bound to the biological substance such as a protein or nucleic acid to be labeled. Examples of the biologically relevant binding substance include antibodies that bind specifically to particular proteins (primary antibodies); antibodies that bind to the primary antibodies (secondary antibodies); antibodies that bind to the secondary antibodies (tertiary antibodies); nucleic acid probes that hybridize to nucleic acids having particular base sequences; biotin and avidin (including the native avidin as well as avidin analogs such as streptavidin and neutravidin); hapten (such as dinitrophenol, digoxigenin, and FITC (fluorescein isothiocyanate)); and anti-hapten antibodies.

(Method for Producing Labeling Agent)

The method for producing the labeling agent in which phosphor integrated dots nanoparticles are linked to a biologically relevant binding substance is not limited, and a variety of known methods may be used. For example, phosphor integrated dots nanoparticles to which a biologically relevant binding substance is covalently bound can be prepared by introducing reactive functional groups to both the surface of the phosphor integrated dots nanoparticles and the biologically relevant binding substance using reagents or the like, and then binding these functional groups to each other. Alternatively, instead of performing the direct covalent bonding of the biologically relevant binding substance to the phosphor integrated dots nanoparticles, a linker having a certain molecular length, preferably a linker containing a hydrophilic macromolecule such as polyethylene glycol, may be interposed between the biologically relevant binding substance and the phosphor integrated dots nanoparticles (that is, between the functional groups contained in these). Examples of the combination of the reactive functional groups include the combinations of an NHS ester group—an amino group; and a thiol group—a maleimide group. For example, phosphor integrated dots nanoparticles modified by streptavidin can be obtained by (i) introducing an amino group on the surface of the phosphor integrated dots nanoparticles using a silane coupling agent; (ii) reacting N-hydroxysuccinimidyl-S-acetylthioacetate with streptavidin to introduce an acetyl-protected thiol group to an end of an amino group contained in streptavidin; (iii) providing, as a cross-linker, a polyethylene glycol chain having at one end an NHS group to be reacted with an amino group, and at the other end a maleimide group to be reacted with a thiol group; (iv) reacting the amino group on the surface of the phosphor integrated dots nanoparticles with the NHS group of the cross-linker to allow covalent bonding; and (v) deprotecting the thiol group of streptavidin, and then reacting it with the maleimide group of the cross-linker.

(Use of Labeling Agent)

The use of the labeling agent of the present invention is not limited, and a variety of uses can be assumed similarly to the known labeling agents. Typically, the labeling agent of the present invention may be used for preparation of pathological specimens, or for fluorescent labeling of a biological substance such as a particular protein or nucleic acid contained in tissue sections. Depending on what kind of biologically relevant binding substance is linked to the phosphor integrated dots nanoparticles, the labeling agent is applicable to a variety of embodiments such as direct labeling of a protein (antigen) or nucleic acid (gene) of interest with the labeling agent, and indirect labeling through reaction between a primary antibody and a secondary antibody, reaction between avidin and biotin, reaction between hapten and an anti-hapten antibody, or the like.

For example, a labeling agent in which streptavidin as a biologically relevant binding substance is linked to phosphor integrated dots nanoparticles can be used as follows. First, a primary antibody is bound to a protein to be fluorescently labeled, and then a biotin-modified secondary antibody is bound to the primary antibody. Subsequently, a labeling agent to which streptavidin is linked is bound to the biotin. Alternatively, a biotin-modified nucleic acid probe may be bound to a nucleic acid (gene) to be fluorescently labeled, and then a labeling agent to which streptavidin is linked may be bound to the biotin. Thus, a labeling agent in which biotin or avidin is linked to phosphor integrated dots nanoparticles can be indirectly bound to a target biological substance through the avidin-biotin bond, thereby allowing fluorescent labeling (avidin-biotin method).

EXAMPLES

[Example 1] Melamine Resin Nanoparticle Containing Hydrophobic Substituent in which Hydrophobic Fluorescent Dye (BODIPY) is Accumulated

[1-1] Production of Melamine Resin Nanoparticle Using Resin Raw Material Containing Hydrophobic Substituent 10 mg of a hydrophobic fluorescent dye "BODIPY 493/503" (Life Technologies) was added to 22 mL of water, and 2 mL of 5% aqueous solution of an emulsifier for emulsion polymerization "Emulgen (registered trademark) 430" (polyoxyethylene oleyl ether; Kao Corporation) was further added thereto. The temperature of the resulting mixture was increased to 70° C. with stirring on a hot stirrer. Thereafter, as a raw material of a melamine resin, a mixed melamine resin raw material containing 0.32 g of a methylated melamine resin (methyl etherified methylol melamine; containing no hydrophobic substituent) "MX-035" (Sanwa Chemical Co., Ltd.) and 0.32 g of a n-butylated melamine resin (butyl etherified methylol melamine; containing a hydrophobic substituent) "L-127-60" (DIC Corporation) was added to the mixture. Further, as a surfactant, 1000 µL of 10% aqueous solution of dodecylbenzenesulfonic acid (Kanto Chemical Co., Inc.) was added to the mixture. The resulting mixture was stirred under heat at 70° C. for 50 minutes, and then the temperature was increased to 90° C., followed by stirring the mixture under heat for 20 minutes, to prepare melamine resin nanoparticles in which the hydrophobic fluorescent dye is accumulated.

The resulting dispersion was centrifuged at 20,000 G for 10 minutes using a centrifuge "Micro Refrigerated Centrifuge 3740" (Kubota Corporation). The supernatant was then removed. Thereafter, in order to remove impurities such as the residual fluorescent dye and resin raw material, washing treatment was carried out by adding ultrapure water and performing ultrasonic irradiation, thereby redispersing the particles. The washing by the centrifugation, the removal of the supernatant, and the redispersion in ultrapure water was repeated five times.

[1-2] Surface Modification of Melamine Resin Nanoparticle

In 1.5 mL of ethanol, 0.1 mg of melamine resin nanoparticles obtained by the above process were dispersed, and 2

μL of aminopropyltrimethoxysilane (LS-3150, manufactured by Shin-Etsu Chemical Co., Ltd.) was added thereto, followed by allowing the reaction to proceed for 8 hours, to perform surface amination treatment for conversion of hydroxyl groups present on the surface of the resin particles into amino groups.

Subsequently, using phosphate-buffered saline (PBS) supplemented with 2 mM ethylene diamine tetraacetic acid (EDTA), the concentration of the melamine resin nanoparticle dispersion after the surface amination treatment was adjusted to 3 nM. To the dispersion after the concentration adjustment, SM(PEG) 12 (succinimidyl-[(N-maleimidopropionamide)-dodecaethylene glycol]ester; manufactured by Thermo Scientific) was added to a final concentration of 10 mM, and the resulting mixture was reacted at 20° C. for 1 hour to prepare melamine resin nanoparticles (particles 1) modified with a PEG chain having a maleimide group at its terminus.

The resulting dispersion was centrifuged at 10,000 G for 20 minutes using the above centrifuge. After removal of the supernatant, PBS supplemented with 2 mM EDTA was added thereto, and then the precipitate was dispersed, followed by performing centrifugation again. Washing by the same procedure was carried out three times.

[1-3] Preparation of Thiol-Modified Streptavidin

After reacting streptavidin (Wako Pure Chemical Industries, Ltd.) with N-succinimidyl-S-acetylthioacetate (abbreviation: SATA), gel filtration was carried out to prepare a thiol-modified streptavidin.

[1-4] Preparation of Labeling Agent

The melamine resin nanoparticle modified with a PEG chain having a maleimide group at its terminus, and the thiol-modified streptavidin, obtained in the above process were mixed in PBS supplemented with 2 mM EDTA, and reacted at room temperature for 1 hour to bind the maleimide group in the melamine resin nanoparticle to the thiol group in the streptavidin. Thereafter, the reaction was stopped by addition of 10 mM mercaptoethanol. The obtained dispersion was concentrated with a 0.65-μm centrifugal filter, and unreacted streptavidin and the like were removed using a purification gel filtration column, to prepare a labeling agent (labeling agent 1) composed of hydrophobic fluorescent dye-accumulated melamine resin nanoparticles to which streptavidin is linked through a PEG chain.

[Example 2] Melamine/Benzoguanamine Copolymer Nanoparticle Containing Hydrophobic Substituent in which Hydrophobic Fluorescent Dye (BODIPY) is Accumulated Melamine/benzoguanamine copolymer nanoparticles (particles 2) were prepared in the same manner as in Example 1 except that, in the Step [1-1], 0.15 g of a methylated melamine resin (methyl etherified methylol melamine; containing no hydrophobic substituent) "MX-035" (Sanwa Chemical Co., Ltd.) and 0.55 g of a butylated benzoguanamine resin (butyl etherified methylol benzoguanamine; containing a hydrophobic substituent) "TD-126" (DIC Corporation) were used instead of the above mixed melamine resin raw material. Subsequently, a labeling agent (labeling agent 2) composed of hydrophobic fluorescent dye-accumulated melamine/benzoguanamine copolymer nanoparticles to which streptavidin is linked through a PEG chain was prepared.

[Example 3] Xylene/Phenol Copolymer Nanoparticle in which Hydrophobic Fluorescent Dye (BODIPY) is Accumulated 10 mg of a hydrophobic fluorescent dye "BODIPY 493/503" (Life Technologies) was added to 20 mL of water, and as a raw material of a xylene/phenol copolymer, 1000 μL of 10% aqueous solution of dodecylbenzenesulfonic acid (Kanto Chemical Co., Inc.) in which 0.80 g of a phenol-modified resol-type xylene resin "Nikanol PR-1440M" (Fudow Co., Ltd., phenol-modified resol-type methylol xylene; although this is a mixture of oligomers having different reaction modes, see the following Formula (13) as an example) and 0.20 g of phenol are preliminarily dissolved was added thereto. The resulting mixture was stirred under heat at 90° C. for 20 minutes, and then heated at 125° C. for 5 minutes using an autoclave, to prepare xylene/phenol copolymer nanoparticles (particles 3) in which the hydrophobic fluorescent dye is accumulated. Thereafter, a labeling agent (labeling agent 3) composed of hydrophobic fluorescent dye-accumulated xylene/phenol copolymer nanoparticles to which streptavidin is linked through a PEG chain was prepared in the same manner as in Example 1.

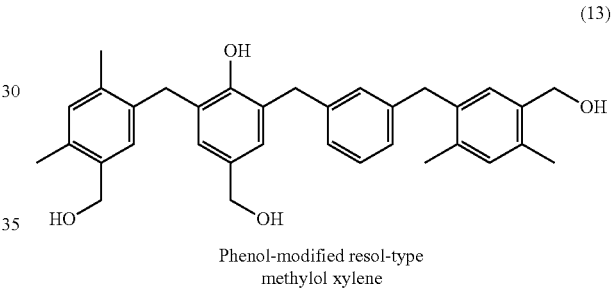

(13)

Phenol-modified resol-type methylol xylene

[Example 4] Melamine Resin Nanoparticle Containing Hydrophobic Substituent in which Semiconductor Quantum Dot is Accumulated Melamine/benzoguanamine copolymer nanoparticles (particles 4) were prepared in the same manner as in Example 1 except that, in the Step [1-1], 200 μL of a semiconductor quantum dot "Qdot (registered trademark) 545 ITK Organic Quantum Dots" (Invitrogen) was used instead of the fluorescent dye, and then a labeling agent (labeling agent 4) composed of a semiconductor quantum dot-accumulated melamine resin to which streptavidin is linked through a PEG chain was prepared.

[Comparative Example 1] Melamine Resin Nanoparticle Containing No Hydrophobic Substituent Melamine resin nanoparticles (particles 5) were prepared in the same manner as in Example 1 except that, in the Step [1-1], 0.65 g of a methylated melamine resin (methyl etherified methylol melamine; containing no hydrophobic substituent) "MX-035" (Sanwa Chemical Co., Ltd.) was used instead of the above mixed melamine resin material. Subsequently, a labeling agent (labeling agent 5) composed of melamine resin nanoparticles to which streptavidin is linked through a PEG chain was prepared.

[Evaluation 1] Evaluation of Fluorescence Intensities of Labeling Agent Dispersions Using each of the labeling agents 1 to 4 and the labeling agent 5 prepared in Examples 1 to 4 and Comparative Example 1, an aqueous dispersion at a concentration of 0.1 nM was prepared, and its fluorescence intensity was measured using a spectrophotofluorometer "F-7000" (Hitachi High-Tech Science Corporation).

The results are shown in the following table. The fluorescence intensities of labeling agent 1 (Example 1), which was prepared using a melamine resin containing a hydrophobic substituent, and labeling agent 2 (Example 2), which was prepared using a melamine/benzoguanamine copolymer containing a hydrophobic substituent, were much higher than the fluorescence intensity of labeling agent 5 (Comparative Example 1), which was prepared using a melamine resin containing no hydrophobic substituent. These results suggest that the accumulated amounts of the hydrophobic fluorescent dye (BODIPY 493/503) in the melamine resin nanoparticles (particles 1) constituting labeling agent 1 and the melamine/benzoguanamine copolymer nanoparticles (particles 2) constituting labeling agent 2 are much larger than the accumulated amount in the melamine resin nanoparticles of Comparative Example 1 (particles 5). It is thus assumed that hydrophobic interaction between the hydrophobic fluorescent dye and the hydrophobic substituents of the melamine resins contributes to the accumulation of the hydrophobic fluorescent dye.

Similarly to labeling agents 1 and 2, labeling agent 3 (Example 3), which was prepared using the xylene/phenol copolymer containing a benzene ring (phenyl group) as a hydrophobic substituent, showed a fluorescence intensity much higher than that of labeling agent 5 (Comparative Example 1). It is thus assumed that accumulation of the hydrophobic fluorescent dye could be achieved also with the xylene/phenol copolymer particles (particles 3).

Similarly, in the case of labeling agent 4 (Example 4), which was prepared using a hydrophobic semiconductor quantum dot instead of a hydrophobic fluorescent dye, it is assumed that accumulation of the hydrophobic semiconductor quantum dot to the melamine resin particles (particles 4) containing a hydrophobic substituent could be achieved. It should be noted that, since one particle of semiconductor quantum dot has a higher fluorescence intensity than one molecule of fluorescent dye, the labeling agent (particles) of Example 4, in which a semiconductor quantum dot is accumulated, emitted fluorescence with an even higher intensity than the labeling agents (particles) of Examples 1 to 3, in which a fluorescent dye is accumulated.

TABLE 1

| | Example 1 | Example 2 | Example 3 | Example 4 | Comparative Example 1 |
|---|---|---|---|---|---|
| Particle/Labeling agent | Particle 1/Labeling agent 1 | Particle 2/Labeling agent 2 | Particle 3/Labeling agent 3 | Particle 4/Labeling agent 4 | Particle 5/Labeling agent 5 |
| Fluorescent substance | BODIPY 493/503 | BODIPY 493/503 | BODIPY 493/503 | Qdot545 ITK Organic Quantum Dots | BODIPY 493/503 |
| Resin | Melamine resin | Melamine-benzoguanamine copolymer | Xylene-phenol copolymer | Melamine resin | Melamine resin |
| Raw material | | | | | |
| containing a hydrophobic substituent | Butyl etherified methylol melamine | Butyl etherified methylol benzoguanamine | Phenol-modified resol-type methylol xylene + phenol | Butyl etherified methylol melamine | — |
| not containing a hydrophobic substituent | Methyl etherified methylol melamine | Methyl etherified methylol melamine | — | Methyl etherified methylol melamine | Methyl etherified methylol melamine |
| Fluorescence intensity (relative ratio taken Comparative Example 1 as 1) | 150 | 250 | 130 | 7000 | 1 |

[Evaluation 2] Evaluation of Fluorescence Intensities of Labeling Agents Used for Staining of Tissue Sections, after Long-Term Storage Using each of labeling agent 1 and labeling agent 2, which were prepared in Example 1 and Example 2, and using as a tissue array slide a slide having spots of breast cancer tissue sections arranged on an array (US Biomax Inc., BR243), the tissue sections were stained by the following procedure to provide an observation slide.

(i) According to conventional methods, the tissue array slide was subjected to deparaffinization treatment, hydrophilization treatment, and antigen activation treatment. Thereafter, the tissue array slide was washed with PBS.

(ii) An anti-HER2 mouse monoclonal antibody solution diluted to 0.05 nM with PBS buffer supplemented with 1% BSA was dropped on the tissue sections, and the reaction was allowed to proceed for 2 hours. Thereafter, the tissue array slide was washed with PBS.

(iii) A biotin-labeled anti-mouse IgG antibody solution diluted with PBS buffer supplemented with 1% BSA was dropped on the tissue sections, and the reaction was allowed to proceed for 30 minutes. Thereafter, the tissue array slide was washed with PBS.

(iv) A solution of each labeling agent diluted to 0.1 nM with PBS buffer supplemented with 1% BSA was dropped on the tissue sections, and the reaction was allowed to proceed for 2 hours. Thereafter, the tissue array slide was washed with PBS.

(v) Mayer's hematoxylin solution was dropped on the tissue sections, and the reaction was allowed to proceed for 5 minutes to perform hematoxylin staining (nuclear staining). Thereafter, the tissue array slide was washed with running water (at about 45° C.) for 3 minutes.

(vi) An aqueous mounting agent "Prolong gold" (Life Technologies) was dropped on the tissue sections, and the tissue sections were covered with a cover glass for mounting. The thus prepared tissue array slide was provided as an observation slide.

First, immediately after the embedding treatment, the thus prepared observation slide was irradiated with excitation light using an inverted fluorescence microscope (Carl Zeiss) to cause emission of fluorescence, and a fluorescence image was obtained (excitation light wavelength, 480 to 520 nm; fluorescence wavelength, 530 to 560 nm; irradiation energy in the vicinity of the center of the visual field, 900 W/cm$^2$; exposure time, 4000 microseconds). Thereafter, the observation slide was stored in a refrigerator for 6 months, and then a fluorescence image was obtained again in the same manner as described above.

For each of the fluorescence images obtained immediately after the embedding or after 6 months of storage, the brightness of each pixel in the image was calculated using image analysis software "Image-J", and the average brightness in the area fluorescently stained with the labeling agent was calculated to determine the "fluorescence intensity". Thereafter, the relative value of the fluorescence intensity after the 6 months of storage with respect to the fluorescence intensity immediately after the embedding was calculated.

The results are shown in the following table. Although labeling agent 1 of Example 1 can be said to have maintained a relatively high fluorescence intensity for 6 months, labeling agent 2 of Example 2 can be said to have an even better ability to maintain the fluorescence intensity. This is thought to be due to the following reason. Since the butyl etherified methylol benzoguanamine constituting the matrix of particle 2 of Example 2 contains a phenyl group (benzene ring) and a butyl group as a hydrophobic substituent, in addition, π-π interaction (stacking interaction) occurs between the phenyl group (benzene ring) and an aromatic ring which is the skeleton of the fluorescent dye (BODIPY 493/503). Therefore, compared to particle 1 of Example 1, which contains only a butyl group as a hydrophobic substituent, particle 2 of Example 2 has a stronger interaction between the matrix and the fluorescent dye, so that reducing the release of the fluorescent dye and degradating the fluorescent dye caused by infiltration of water into the particle can be suppressed for a long period.

TABLE 2

|  | Example 1 | Example 2 |
| --- | --- | --- |
| Particle/Labeling agent | Particle 1/ Labeling agent 1 | Particle 2/ Labeling agent 2 |
| Fluorescent substance | BODIPY 493/503 | BODIPY 493/503 |
| Resin | Melamine resin | Melamine-benzoguanamine copolymer |
| Raw material |  |  |
| containing a hydrophobic substituent | Butyl etherified methylol melamine | Butyl etherified methylol benzoguanamine |
| not containing a hydrophobic substituent | Methyl etherified methylol melamine | Methyl etherified methylol melamine |
| Fluorescence intensity on an observation slide after 6 months of storage (relative ratio taken the initial value as 100) | 70 | 90 |

The invention claimed is:

1. Phosphor integrated dots nanoparticles comprising a hydrophobic fluorescent substance accumulated therein and a thermosetting resin as a matrix, said thermosetting resin containing a structural unit formed from a raw material containing a hydrophobic substituent, said hydrophobic fluorescent substance being accumulated in said nanoparticles at least by hydrophobic interaction with the hydrophobic substituent of said thermosetting resin.

2. The phosphor integrated dots nanoparticles according to claim 1, wherein said hydrophobic fluorescent substance is accumulated in said nanoparticles further by stacking interaction with the hydrophobic substituent of said thermosetting resin.

3. The phosphor integrated dots nanoparticles according to claim 1, wherein said hydrophobic substituent is at least one selected from the group consisting of $C_4$-$C_{10}$ linear, branched, or cyclic alkyl groups, alkenyl groups, and alkynyl groups each of which optionally has a substituent(s); and $C_6$-$C_{15}$ aryl groups and heteroaryl groups each of which optionally has a substituent(s).

4. The phosphor integrated dots nanoparticles according to claim 3, wherein said hydrophobic substituent is a phenyl group.

5. The phosphor integrated dots nanoparticles according to claim 1, wherein said thermosetting resin is a thermosetting resin containing both a structural unit formed from a raw material containing a hydrophobic substituent and a structural unit formed from a raw material containing no hydrophobic substituent.

6. The phosphor integrated dots nanoparticles according to claim 1, wherein said thermosetting resin contains a structural unit(s) formed from one or more raw materials including at least one raw material having a hydrophobic substituent selected from the group consisting of melamine, guanamine, aniline, urea, phenol, xylene, and derivatives thereof.

7. The phosphor integrated dots nanoparticles according to claim 6, wherein said thermosetting resin contains a structural unit(s) formed from at least one raw material selected from the group consisting of butyl etherified methylol melamine, benzoguanamine, butyl etherified methylol guanamine, and butyl etherified methylol benzoguanamine.

8. The phosphor integrated dots nanoparticles according to claim 1, wherein said hydrophobic fluorescent substance is a BODIPY (registered trademark)-based dye molecule, FM-based dye molecule, oxazine-based fluorescent dye molecule, azobenzene-based fluorescent dye molecule, rhodamine-based dye molecule, squarylium-based dye molecule, pyrene-based dye molecule, or perylene-based dye molecule.

9. A labeling agent comprising the phosphor integrated dots nanoparticles according to claim 1 and a biologically relevant binding substance linked to the surface thereof.

\* \* \* \* \*